United States Patent [19]
Ferguson et al.

[11] Patent Number: 4,758,672
[45] Date of Patent: * Jul. 19, 1988

[54] PROCESS FOR PREPARING NAPHTHENIC ACID 1,2-IMIDAZOLINES

[75] Inventors: Sam Ferguson, Sugar Land; Darrel D. Reese, Richmond, both of Tex.

[73] Assignee: Nalco Chemical Company, Naperville, Ill.

[ * ] Notice: The portion of the term of this patent subsequent to May 20, 2003 has been disclaimed.

[21] Appl. No.: 51,877

[22] Filed: May 18, 1987

[51] Int. Cl.$^4$ ............ C07D 233/18; C07D 233/10; C07D 233/16
[52] U.S. Cl. .................... 548/347; 548/352
[58] Field of Search ............ 548/347, 353, 352

[56] References Cited

U.S. PATENT DOCUMENTS

| Re. 23,227 | 5/1950 | Blair et al. | 548/347 X |
| 2,018,758 | 10/1935 | Ellis | 252/51.5 R |
| 2,152,720 | 4/1939 | Yabroff | 208/232 |
| 2,152,723 | 4/1939 | Yabroff | 208/232 |
| 2,215,864 | 9/1940 | Waldmann et al. | 548/347 |
| 2,279,277 | 4/1942 | Shoemaker | 208/177 |
| 2,355,837 | 8/1944 | Wilson | 548/352 |
| 2,424,158 | 7/1947 | Fuqua et al. | 208/263 |
| 2,468,180 | 4/1949 | De Groote et al. | 548/353 X |
| 2,701,783 | 2/1955 | Long et al. | 208/263 |
| 2,769,767 | 11/1956 | Fierce et al. | 208/263 |
| 2,769,768 | 11/1956 | Fierce et al. | 208/263 |
| 2,797,188 | 6/1957 | Taylor et al. | 208/236 |
| 2,808,431 | 10/1957 | Fierce | 562/511 |
| 2,878,181 | 3/1959 | Ayers et al. | 208/263 |
| 2,956,946 | 10/1960 | King et al. | 208/263 |
| 3,176,041 | 3/1965 | Ayers et al. | 562/511 |
| 3,736,098 | 5/1973 | Kataoka et al. | 548/353 X |
| 3,997,469 | 12/1976 | Howle | 252/392 |
| 4,430,196 | 2/1984 | Hiu | 208/47 |
| 4,589,979 | 5/1986 | Ferguson et al. | 208/263 |

OTHER PUBLICATIONS

*Chemical Abstracts*, 84: 121718h (1976) [Shim, J. et al., *Sumyv Konghak Hoej*, 1975, 12(3), 109–19].
The Naphthenic acids in Kirt-Othmer's Encyclopedia of Chemical Technology, 3rd Edition, vol. 15, John Wiley & Sons, 1981, pp. 749–753.

Primary Examiner—Richard A. Schwartz
Attorney, Agent, or Firm—John G. Premo; Anthony L. Cupoli; Donald G. Epple

[57] ABSTRACT 1,2-imidazolines are prepared by reacting gas oils containing naphthenic acid with polyamines. This reaction, in addition to forming imidazolines, reduces the acidity of the starting gas oils.

1 Claim, No Drawings

PROCESS FOR PREPARING NAPHTHENIC ACID 1,2-IMIDAZOLINES

INTRODUCTION

U.S. Pat. No. 4,589,979, which is incorporated herein by reference, discloses a method for neutralizing the organic acidity in heavy gas oils. The invention is described in this patent as follows:

"The invention comprises a method of neutralizing the organic acidity in heavy gas oils to produce a neutralization number less than 1.0 whereby they are rendered suitable as lube oil feed stocks which comprises treating said heavy gas oils with a neutralizing amount of monoethanolamine to form an amine salt with the organic acids and then heating the thus-neutralized heavy gas oil at a temperature and for a time sufficient to convert the amine salts to amides.

"The amount of monoethanolamine necessary to produce neutralization of a heavy gas oil which has a neutralization number greater than 1.0 can best be determined by using titration techniques or by trial and error.

"As indicated, after the amine has been added to the oil and salt formation occurs, the salts should be converted substantially to their amides. This can be done at temperatures about 25° F. greater than the boiling point of water for a period of time ranging over several days or higher temperatures can be employed and shorter reaction times used. Typically, if one were to heat the salt product at about 400°–500° F. for between 1–2 hours, the amide formation would take place."

The organic acidity present in the heavy gas oils are primarily naphthenic acids.

The present invention relates to 1-2 substituted imidazolines produced by a variation of the above described process as compositions of matter.

THE NAPHTHENIC ACIDS

Naphthenic acids are described in Kirk-Othmer's *Encyclopedia of Chemical Technology*, Third Edition, Volume 15, John Wiley & Sons, 1981, the disclosure of which is incorporated herein by reference.

The naphthenic acids obtained from petroleum and its distillates have hydrocarbon components corresponding generally to the hydrocarbon components of petroleum or its distillates from which they were derived. Preferred sources are the naphthenic acids found in gas oils, particularly heavy gas oils.

The Amines

The starting amines have the structural formula:

Formula I $$H_2N-(CH_2CH-X)_nH$$
$$\phantom{H_2N-(CH_2C}|$$
$$\phantom{H_2N-(CH_2CH-X)}R_1$$

where
$R_1$ is H or Me,
X is chosen, at each occurrence, from O or NH, and
n is a small whole number of from 1–10.
In the above formula, when X is O, n is preferably 1. When X is NH, n is preferably 2 or more.

In addition to the structures defining the starting amines above, it is also understood that the formulas above also represent linear, branched and cyclic congenors of the structures mentioned above. For example, these starting amines may contain such compounds as aminoethyl piperazine, triethylene tetramine, diethylene triamine, and other structures which are branched or cyclic congenors of the above formulas. A preferred material is a commercially available compound or mixture of compounds which contain about 60 weight percent amino ethyl piperazine, about 25 weight percent triethylene tetramine, about 2 weight percent diethylene triamine, and about 12 weight percent of other admixtures of linear, branched and cyclic congenors of the above defined structures.

The 1,2 Imidazolines

The 1,2 substituted imidazolines of the invention have the formula:

Formula II $$R-C\begin{array}{c}N-CH_2\\ \phantom{x}\\ N-CH\\ |\phantom{xx}|\\ Y\phantom{x}R_1\end{array}$$

where R is the hydrocarbon portion of a naphthenic acid of the type previously described, Y is H, $$(CH_2CHX)_nH,$$
$$\phantom{(CH_2C}|$$
$$\phantom{(CH_2CHX)}R_1$$

or $$\begin{array}{c}R\\|\\C=O\\|\\NH\\|\\(CH_2CHX)_{n-1}CH_2CH\\\phantom{xxxxxx}|\phantom{xxxxxxxx}|\\\phantom{xxxxxx}R_1\phantom{xxxxxxx}R_1\end{array}$$

and $R_1$ and X have the values previously described in Formula I. n is 1–10.

The 1,2 substituted imid azolines of our invention may also include amido dimers of the above imidazolines, such that formulas represented by Formula III can be formed.

Formula III where R is the hydrocarbon portion of a naphthenic acid and $R_1$, x and n have the above values.

The imidazolines of this invention can also be any admixture of any components represented by the above formulas.

The steps described in U.S. Pat. No. 4,589,979 are generally followed except that the amine salts of the naphthenic acids are heated to an elevated temperature sufficient to remove 2 moles of water per mole of naphthenic acid. This dehydration step causes the formation of 1,2 substituted imidazolines. With respect to more specifics relative to the necessary reaction conditions, please refer to U.S. Pat. No. 2,355,837, the disclosure of which is incorporated herein by reference, and made a part hereof.

After the reaction is completed and the 1,2 substituted imidazolines formed, they may potentially be separated from the heavy gas oils by using conventional separation techniques such as solvent extraction which may employ either organic solvents or water. The most preferable method of extracting and isolating the 1,2 substituted imidazolines comprises the vacuum distillation of the gas oil from the 1,2 substituted imidazolines contained therein.

A typical method for preparing the 1,2 substituted imidazolines is set forth below:

A virgin gas oil was selected from a refinery located in the southern part of the United States. The neutralization number of this gas oil was 3.54. The neutralization number was determined using the well-known ASTM procedure D-974.

To determine the effectiveness of different amines at lowering the neutralization number, a weighed amount of the test vacuum gas oil and the additive were refluxed at between 450°–500° F. for 4 hours. These reaction conditions are believed to have converted the salt formed by neutralization to the 1,2 substituted imidazoline, the effects of which were to reduce corrosion rates on mild steels exposed to gas oils containing naphthenic acids.

Using this procedure, one would heat the oil containing the naphthenic acid with any of the following amines:

Polyamine Bottoms*
Tetraethylene Pentamine**
Aminoethyl ethanol amine
Ethylenediamine
Diethylenetriamine \* A mixture of aliphatic and heterocyclic amines with boiling range between 410°–465° F., Sp.G. ranging between 0.98–1.09 with multiple amine substituents.

\*\* A mixture containing: 65 weight percent of major isomers
1. linear triethylene pentamine
2. linear tetra ethylene pentamine
3. amino ethyl tris—amino ethylamine
4. amino ethyl diamino ethyl piperazine
5. aminoethyl piperazino ethyl ethylene diamine
6. piperazino ethyl diamino ethyl amine
7. bis-piperazino ethyl amine, and 25 weight percent of the following major isomers:
   (1) linear triethylene tetramine
   (2) tris-amino ethylamine
   (3) piperazino ethyl ethylene diamine
(4) bis-aminoethyl piperazine, and about 10 weight percent of:
   1. pentaethylene hexamine
   2. other linear, branched, and cyclic congenors of similar amino structures.

The heating would be at a temperature ranging between 400°–500° F. or above for a period of time sufficient to remove two moles of water for each mole of acid, and would be at a pressure necessary to accomplish the desired reactions.

The gas oil containing the 1,2 substituted imidazolines would then be vacuum distilled and the 1,2 substituted imidazolines residue would be recovered.

Having thus described our invention, we claim:

1. A method of producing the naphthenic acid 1,2-imidazoline having the formula:

$$R-C \underset{\underset{Y}{\overset{}{N}}-\underset{R_1}{\overset{}{CH}}}{\overset{N=CH_2}{\diagup}}$$

where R is the hydrocarbon portion of a petroleum or a petroleum fraction naphthenic acid, Y is H, $$(CH_2\underset{R_1}{\overset{}{C}}HX)_nH,$$

or, $$\begin{array}{c} R \\ | \\ C=O \\ | \\ NH \\ | \\ +CH_2\underset{R_1}{\overset{}{C}}HX)_{n-1}CH_2\underset{R_1}{\overset{}{C}}H \end{array}$$

$R_1$ is H or Me
X is chosen, at each occurrence, from O or NH, and
n is a number having the value of 1–9 which comprises reacting an amine of the formula $$H_2H-(CH_2\underset{R_1}{\overset{}{C}}H-X)_nH$$

where
$R_1$ is H or Me,
x is chosen, at each occurrence, from O or NH, and
n is a small whole number of from 1–10,
with a petroleum fraction containing naphthenic acid to form a salt and then heating the petroleum fraction containing the naphthenic acid amine salt to a temperature of at least 25° F. greater than the boiling point of water for a time sufficient to convert the amine salts to the 1,2 imidazoline.

\* \* \* \* \*